(12) United States Patent
Cattell et al.

(10) Patent No.: US 7,027,629 B2
(45) Date of Patent: Apr. 11, 2006

(54) METHOD OF EXTRACTING LOCATIONS OF NUCLEIC ACID ARRAY FEATURES

(75) Inventors: Herbert F. Cattell, Mountain View, CA (US); Andreas N. Dorsel, Menlo Park, CA (US); John W. Sadler, Belmont, CA (US); Nicholas M. Sampas, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/238,922

(22) Filed: Sep. 9, 2002

(65) Prior Publication Data

US 2003/0059094 A1 Mar. 27, 2003

Related U.S. Application Data

(63) Continuation of application No. 09/435,462, filed on Nov. 5, 1999, now abandoned.

(51) Int. Cl.
*G06K 9/00* (2006.01)

(52) U.S. Cl. ............... 382/128; 382/129; 382/141

(58) Field of Classification Search ........ 382/128–129, 382/133–134, 256, 257, 258, 259, 266, 141, 382/145, 151, 149
See application file for complete search history.

(56) References Cited

U.S. PATENT DOCUMENTS

| 4,707,647 | A | * | 11/1987 | Coldren et al. ........... 382/151 |
| 5,019,997 | A | * | 5/1991 | Haller ........................ 716/21 |
| 5,086,319 | A | * | 2/1992 | Carolan ..................... 399/396 |
| 5,581,487 | A | | 12/1996 | Kelly et al. |
| 5,721,435 | A | | 2/1998 | Troll |
| 5,744,305 | A | | 4/1998 | Fodor et al. |
| 5,801,970 | A | | 9/1998 | Rowland et al. |
| 5,812,272 | A | | 9/1998 | King et al. |
| 5,834,758 | A | | 11/1998 | Trulson et al. |
| 5,837,475 | A | | 11/1998 | Dorsel et al. |
| 5,861,242 | A | | 1/1999 | Chee et al. |
| 6,258,536 | B1 | * | 7/2001 | Oliner et al. .................. 435/6 |
| 6,269,322 | B1 | * | 7/2001 | Templeton et al. ........ 702/150 |
| 6,345,115 | B1 | * | 2/2002 | Ramm et al. ............... 382/133 |
| 6,349,144 | B1 | | 2/2002 | Shams |
| 6,674,882 | B1 | | 1/2004 | Shams |

FOREIGN PATENT DOCUMENTS

| WO | WO 99/08233 | 2/1999 |
| WO | WO 01/06395 | 1/2001 |

OTHER PUBLICATIONS

A. Kuklin et al., "High throughput screening of gene expression signatures," 2000, Genetica 108, pp. 41-46.
R.C.Y. Cheung and Christopher J.S. deSliva, "Analysis of Gene Microarray Images," 1999, IEEE, pp. 627-632.

* cited by examiner

*Primary Examiner*—Jose L. Couso
*Assistant Examiner*—Tom Y. Lu

(57) ABSTRACT

Methods for correcting systematic errors in the measured position of deposited features of a nucleic acid array on a substrate. Systematic errors are modeled by an algorithmic model based on measuring the positions (and possibly other properties) of a subset of the features, and a model is constructed for predicting deviations in feature position from an ideal grid. Deviations arising in the deposition process, the scanning process, or both may be corrected.

14 Claims, 2 Drawing Sheets

METHOD OF EXTRACTING LOCATIONS OF NUCLEIC ACID ARRAY FEATURES

RELATED U.S. APPLICATION DATA

This application is a continuation of U.S. application Ser. No. 09/435,462 filed on Nov. 5, 1999 now abandoned.

FIELD OF THE INVENTION

This application pertains to methods and apparatus for determining locations of features in a surface array, and to methods and apparatus for compensating for systematic errors in the determination of feature positions.

BACKGROUND OF THE INVENTION

The rapid pace of genetic research has required the development of new research tools to efficiently determine both genotype and gene expression levels in cellular organisms. "Gene chips" which contain arrays of short DNA or RNA chains in an array of sequences bound to a substrate (usually glass) are now commercially available. The chip is indexed so that the particular sequence bound in any area is known (or, in the case of cDNA, at least the cell line is known); a region having a homogeneous composition is referred to as a "feature." The chips can be incubated with a target solution containing DNA or RNA bound to a fluorescent tag, allowing the binding of target DNA or RNA to individual features. Such systems can be used for the determination of both genotype and gene expression levels.

In genotype analysis, it is usually merely the presence or absence of binding that must be sensed. If fluorescence is observed above a threshold level in a particular region, binding has occurred and a sequence is identified by consulting the index of DNA or RNA positions on the chip. It is currently necessary for feature sizes to be large enough that their locations can be accurately identified by dead reckoning (possibly based on cued fluorescent features deposited at the same time as the feature array).

A more difficult problem is the quantitative measurement of levels of gene expression using DNA or RNA chip methods. The chemical density of a particular species is generally monotonically related to its level of fluorescence. Thus, the intensity of the fluorescence can be measured to obtain information about the chemical density. A portion of an exemplary chip is shown in FIG. 1. Fluorescence levels may span 2–3 orders of magnitude in some cases; thus, determining the position of both bright and dim signals cannot generally be accomplished by simple calculations, such as thresholding of signal images. A variety of image analysis techniques exist for identifying feature locations for intensity measurement, but most rely on the feature array being perfectly regular, at most being able to make simple linear compensations for small amounts of stretching and rotation.

It is desirable to provide chips having small feature sizes, in order to increase the number of features that can be placed on a single chip. However, as feature sizes decrease, systematic errors in feature deposition and scanning may make accurate feature location by dead reckoning increasingly impractical. It is an object of the present invention to provide a superior system for correlating bright and dim regions of a scanned substrate with known underlying features in order to accurately measure feature intensity and position, thereby obtaining accurate analysis of the underlying signal for each feature.

SUMMARY OF THE INVENTION

In one aspect, the invention comprises a method of determining feature locations on a substrate. Ideal feature locations (the locations in which features would be deposited if no measurable errors existed in the deposition system) are determined, and a source of systematic error in the deposition system is also located. A nonlinear algorithmic model for the error is constructed, and the model is trained by using measured position data for a subset (which may be the whole) of the physical features. The trained model is then used to predict deviations in feature location from the ideal locations. The subset may be selected, for example, by on a criterion based on one or more properties selected from the group consisting of signal strength, feature size, deviation of the position of the feature from a corresponding ideal location, and the distribution of pixel values. The method may further comprise compensating for a second systematic error source (in either deposition or sensing systems) by constructing a second algorithmic model and combining it with the first model. An example model may be based on calculating a characteristic size, shape, and/or offset for all features deposited by a single pin in a multipin deposition system. The algorithmic model(s) may be used to predict the locations of all features, or the measured locations may be used for the subset of features and the model used to predict the positions of only the nonmeasured features.

In a related aspect, the invention includes another method of determining feature locations on a substrate. In this aspect, the invention again comprises determining ideal feature locations on a substrate and further identifying a source of error, this time in the sensing system used to scan the physical features. A nonlinear algorithmic model of the error is constructed, and the sensing system is used to sense certain features whose actual deviations from the ideal feature locations are known. The resulting measurements are used to train the algorithmic model, which can then be used to predict deviations in sensed feature positions from actual positions. The method may further comprise compensating for a second systematic error source (in either deposition or sensing systems) by constructing a second algorithmic model and combining it with the first model. The features whose positions are known may be, for example, fiducial features deposited at the same time as the other features.

In another aspect, the invention includes a method of determining feature locations on a substrate by measuring the locations of the deposited features (for example during the deposition process), and recording the measured location of each feature. The substrate may then be subjected to a process which alters the intensity of an observable property of the features (such as by exposing a DNA chip to RNA bound to a fluorescent species), scanning the substrate to generate a set of pixel data corresponding to the intensity of the observable property, and correlating the pixel data with the recorded locations to determine the intensity of the observable property for each feature. The features may, for example, be constructed in a series of deposition steps, in which the locations of the features are measured after each step. These successively measured locations may then be used to determine the extent of the area which has been subjected to all the deposition steps (i.e., the "sweet spot").

In still another aspect, the invention comprises a method of measuring feature intensities on a substrate, comprising determining the size of the features and the uncertainty in feature placement, and using these data to calculate the size of the smallest area which is known to contain an entire feature. This entire area is then subjected to an intensity measurement to determine the feature intensity.

In yet another aspect, the invention comprises a method of selecting a group of "strong" features, by scanning a substrate to generate a set of pixel data, and then evaluating regions of the pixel data in the vicinity of ideal feature locations by applying a criterion determined by one or more properties of the pixel data selected from the group consisting of pixel magnitude, number of pixels having magnitudes above a threshold value, locations of pixels having magnitudes above a threshold value, and distribution of pixel magnitude values. The pixel data may be prefiltered before applying the selection criterion, for example by smoothing, erosion and/or dilation, outlier rejection, median filtering, and background subtraction.

"Algorithmic models," as that phrase is used herein, are considered to include analytical models, parametric models, and models based on look-up tables. A distinguishing characteristic of an algorithmic model is that a particular input or set of inputs will always give the same output (assuming that the parameters of the model remain constant). A nonlinear algorithmic model is one that cannot be represented by an affine transformation.

"Deposited features," as that phrase is used herein, refers both to features which are deposited essentially in their final form, and to features which are constructed in situ by one or more successive or simultaneous chemical reactions.

BRIEF DESCRIPTION OF THE DRAWING

The invention is described with reference to the several figures of the drawing, in which.

DETAILED DESCRIPTION

Figure 1:
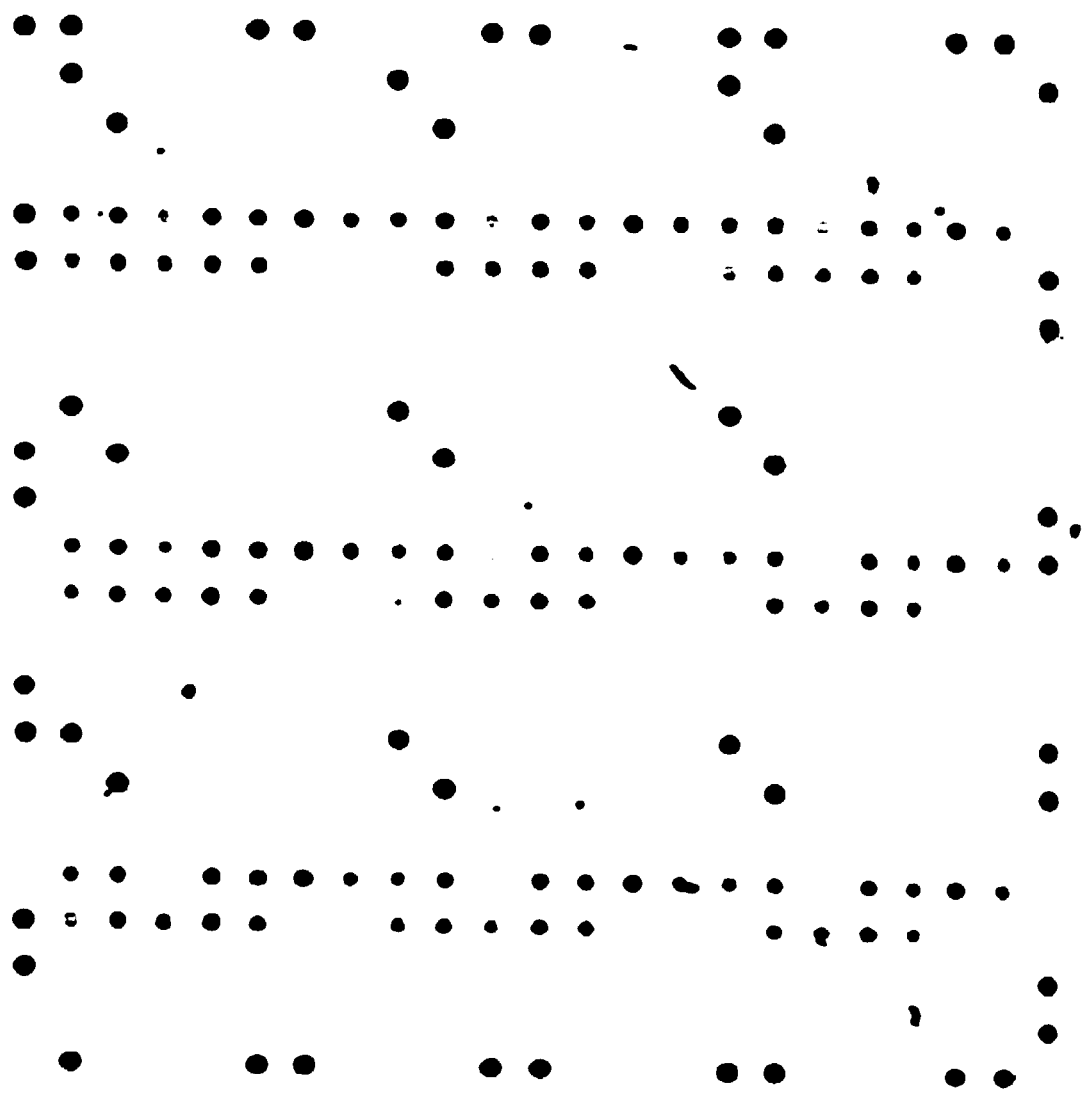
FIG. 1 shows a gene chip used for measurement of gene expression.

While the present invention is described herein with reference to a particular embodiment of sensing feature positions in DNA arrays for genetic sequencing, it will be understood by those skilled in the art that the methods of the invention can be applied to many other image analysis applications. In particular, many other chemical assays (e.g., immunodiagnostic assays) exist for measurement of the relative binding of an analyte species to a number of substrate regions; the methods and systems of the invention may easily be used for such assays. Broader applications may include such diverse systems as machine vision systems for recognition of objects, systems for doping a substrate to construct integrated circuits, and automatic systems for astronomical observation.

The invention comprises methods of compensating for identified sources of systematic error in deposition and/or scanning of feature arrays. Examples of sources of systematic error include registration error in multistep deposition processes; shape, size, and position correlations in features deposited by a single pin in a multipin deposition system; scanner distortions; known or measurable effects of temperature, humidity, line voltage, and other environmental factors; and errors from position feedback devices. Compensation can be made for errors arising from any or all of these sources, or from any other systematic error source which can be measured and/or theoretically modeled. The methods of the invention are applicable to any two-dimensional array geometry, including rectangular arrays, circular arrays, and hexagonal close-packed arrays.

Using the methods of the invention, at least one source of systematic error is first identified. For example, a deposition system will not generally deposit individual features in a perfect array. An algorithmic model is then constructed, using any available data about the error. For example, it may be possible to simply measure the location of some or all of the features after they are deposited on the substrate, but before binding of target RNA or DNA to the substrate. In deposition by solution methods, for example, it is relatively easy to detect the features optically while they are still "wet." Alternatively, salt crystals associated with the DNA deposition may be sensed, or a fluorescent marker which is removable and/or has a different characteristic wavelength from the fluorescent signal that will be used for gene expression measurement may be deposited with the DNA. The positions of every feature may be recorded, or a simpler parametric model may be constructed by which an approximate set of feature positions may be regenerated. A simple example of such a model would be one which records an average offset for all of the features deposited by a single pin. If the number of parameters in the model is small enough, the data may be recorded directly on the chip (e.g., by placing a bar code on the chip carrier); alternatively, the data may be stored separately from the chip itself.

Figure 2A:
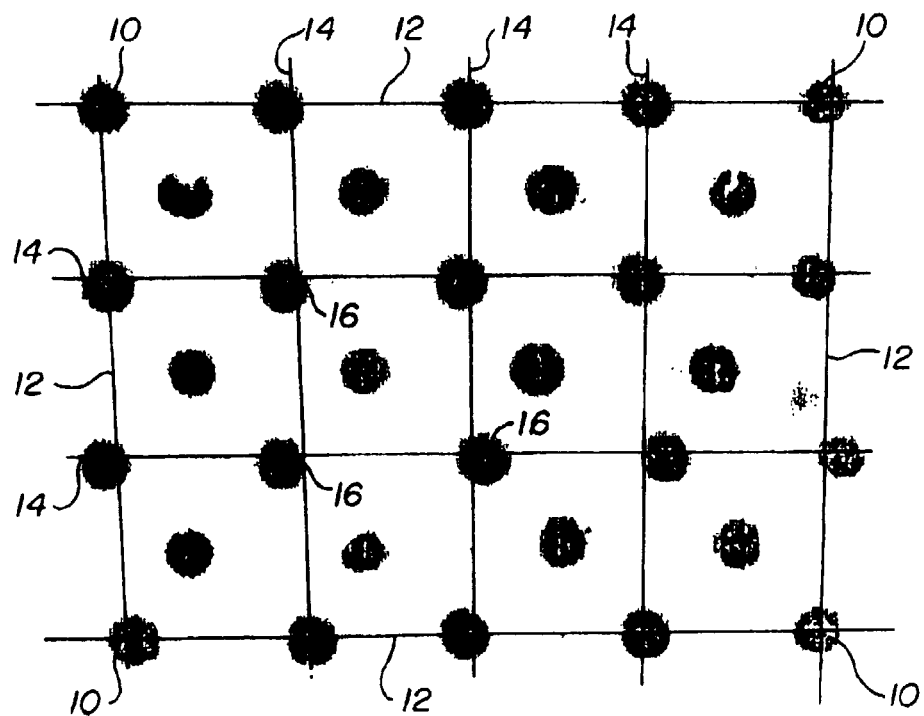
FIGS. 2A and 2B show a feature array with superposed lines illustrating ideal feature locations and modeled feature locations, respectively.
Figure 2B:
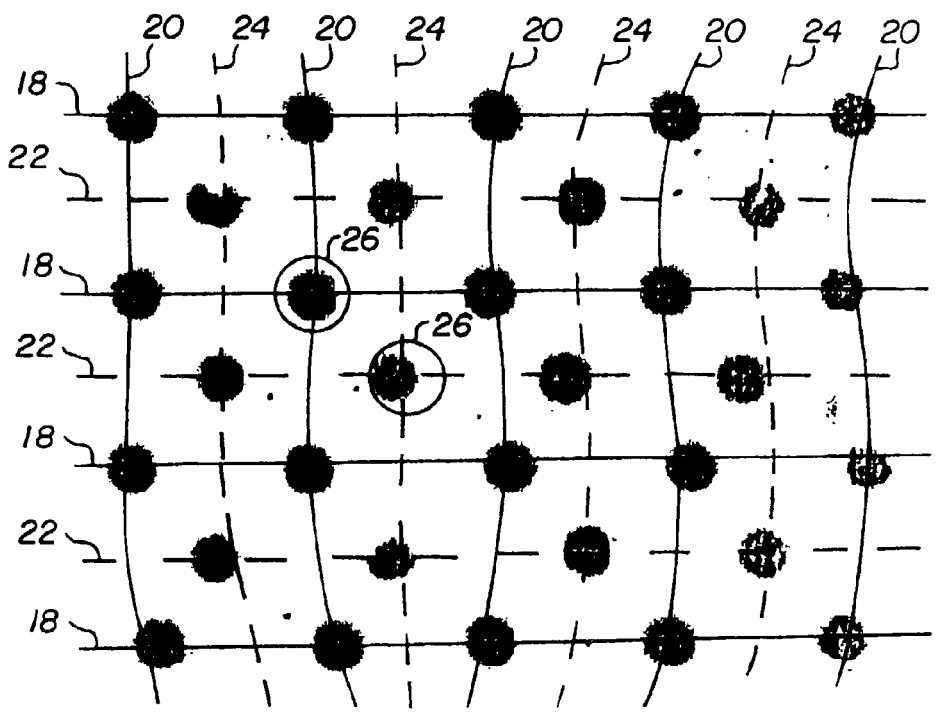

FIGS. 2A and 2B illustrate schematically the application of an algorithmic model for one embodiment of the invention. Both figures show an array of features having roughly constant intensity; these may be, for example, salt crystals or other markers of feature location immediately after deposition. Corner points 10 define a quadrilateral 12. Linear interpolation within the quadrilateral is used to determine ideal feature locations (at the intersections of lines 12, 14) for a subset of the features (in the illustrated case, half of the features). The vicinity of the intersections is examined using 15 known methods to determine the centroids of nearby spots, and an offset 16 is calculated for each spot examined. In the illustrated array, vertical alignment is relatively constant, while horizontal alignment is much more variable. Straight lines 18 are thus used to parametrize the vertical alignment, while curved lines 20 represent the horizontal alignment. The path of the curved lines 20 may be calculated by best fit to an analytical function, by splines, or by any other suitable method. In the illustrated embodiment, linear interpolation is used to find the locations of the remaining points, as illustrated by dashed lines 22, 24. It will be perceived by those skilled in the art that other interpolation or parametrization methods may be used, as well. The locations of regions near the calculated feature locations (indicated by circles 26) may then be stored for later use to calculate feature intensities.

Data may be collected from multiple steps of a deposition/construction process. For example, in in situ construction of DNA sequences, features are built up by successive depositions of individual nucleic acids or short oligonucleotides. Imperfect registration in successive deposition steps means that only an area in the approximate center of the feature is expected to have exactly the desired composition; areas at the periphery will contain shorter nucleotide sequences which are missing certain sequences due to misalignment. The techniques described above for measuring feature positions at intermediate steps in the deposition process may be used to determine the location of the "sweet spot," in which the desired composition is achieved, so that accurate intensity measurements can be made over the entire sweet spot. In addition, the composition at various areas at the periphery of the feature can be inferred, and additional data can be obtained by observing which, if any, of these peripheral areas fluoresce.

Rather than using data collected during the deposition process, it is also possible to use data collected during the scanning process to construct the model. For example, intentionally "bright" features may be deposited in the deposition step, and these features may be used to cue the model. For example, a bright feature may be deposited by each of the deposition pins in a dot-matrix deposition process. The bright features' size, shape, and/or position may then be measured by a simple threshold or edge detection algorithm, and these data may be used to predict variations in the expected location of the other features to be measured.

Alternatively, features anywhere on the substrate which happen to be bright when scanned can be used to train the model. Dead reckoning can be used to estimate the positions of the features; the actual positions of the bright features (which may include features corresponding to "housekeeping genes" whose levels of expression are predictable and known) may then be measured, and an algorithmic model constructed based on comparison of the predicted and measured locations of these features. The model then can be used to predict dim feature locations. In a more refined form of this method further discussed below, not only the brightness but the shape, size, deviation from expected feature location, and pixel brightness distribution can be used to select a set of "strong" features for use in calculating the parameters of the model. In either case, the algorithmic model may either be used for determining the location of all features, or the directly measured data may be used for strong features and the model data for weak features.

Rather than using data collected during the scanning and/or deposition process, known properties of the deposition and/or scanning system can be used to refine the area searched. It is known, for example, to use the largest area which definitely falls within a feature to do intensity measurements (e.g., if spots are 50 µm wide and deposited within ±20 µm, to examine only the center 10 µm area of the spot). Along these lines, the inventors have discovered that better results may be achieved by instead using the smallest area which definitely contains the entire feature (e.g., if spots are 50 µm wide and deposited within ±20 µm, to examine a 90 µm area centered on the expected spot position). It will be apparent that in the absence of background, this method yields substantially better signal-to-noise ratios. In the presence of a uniform background, the background level at which the two methods become equal in performance can be easily calculated and an appropriate method selected. For background that is different inside and outside the feature, a bias in evaluating features can only be avoided to the extent that valid assumptions can be made about feature area and average background level outside and inside the feature. It may be possible to combine this method with the above-described methods of estimating feature size and position using bright feature measurements, in order to reduce the possibility of bias.

It is an advantage of the invention that models of multiple sources of error may be efficiently combined. For example, a model of the scanner (e.g., using the method disclosed in copending and commonly owned Ser. No. 08/999,018, filed Dec. 29, 1997, incorporated by reference herein), and a model of deposition location errors as described above, may easily be "layered" to model both types of systematic error in a single step.

It is a further advantage that relatively complicated models, which need not be invertible, may be used in the methods of the invention. Prior art systems are generally limited to affine (or linear) transformations: that is, they can model rotations and stretching in two directions, but cannot use nonlinear models. (An affine transformation can be completely determined by locating the positions of four corners of a quadrilateral, and linearly interpolating between them). The present invention may use, for example, higher-order polynomial models, other algebraic models, or combinations of analytical models with look-up tables. When models are nonlinear, it should be remembered that the order in which the cascading models are applied becomes significant.

The invention further comprises methods of selecting which features to use for determining parameters for a model. In the simplest such method, a threshold is applied to the scanned image, and dead-reckoning is used to determine which feature each bright spot represents. Centroids of these bright features are then calculated and used to "train" (determine parameters for) the model.

More complicated algorithms than a simple yes/no decision based solely on brightness can be used, however. A criterion for strong/weak features may be based on any combination of signal strength, feature size, deviation of the position of the feature from its nominal location of the center of a set of pixels, and the distribution of pixel values, for example. Instead of dividing features on a simple strong/weak dichotomy, it is also possible to define a "strength" index based on these properties, which is used to assign weights to individual features used to train the model. Various image analysis techniques such as smoothing, erosion and dilation, outlier rejection, median filtering, and/or background subtraction may be used to prefilter the pixel data before applying the strength criterion.

Multiple criteria may also be used, dividing the features into classes of strong/weak, scattered/dense, near/far from expected location, etc. Features chosen by different criteria may be used to determine different parameters in the model, for example.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for determining positions of features having been formed, due to systematic error in a deposition process, on a nucleic acid array on a substrate, the method comprising:

calculating ideal positions of one or more of the features as the one or more features would be placed if the array placement occurred without the systematic error;
identifying a systematic position error of the features;
constructing a general model of the systematic position error;
determining the positions of a subset of the features formed in the array;
refining the general model of the systematic position error to a specific model of the systematic position error using the determined positions of the subset of features;
using the specific model of the systematic position error to predict the position of at least one feature in the array that is not a member of the subset.

2. The method of claim 1 further including selecting a feature for the subset of features based on one or more of:
a magnitude of the signal measured within the feature;
a size of the feature;
distance of a determined position of the feature from a position calculated for the feature; and
distribution of signal strength within the feature.

3. The method of claim 1 further including selecting strong features for the subset of feature, a feature characterized as strong base on one or more of:
an integrated magnitude of a property measured over an area of the feature greater than a threshold value; and
a distribution of magnitudes of a property measured over an area of the feature within a range of distributions corresponding to strong features.

4. The method of claim 3 wherein the property measurement is filtered by one of:
smoothing;
erosion and dilation;
outlier rejection;
median filtering; and
background subtraction.

5. The method of claim 1 wherein the systematic position error is a first systematic position error which results from a first identified source, the method further including:
identifying a second source of systematic position error in deposition of the features;
constructing a general model of the second systematic position error;
refining the general model of the second systematic position error to a specific model of the second systematic position error using the determined positions of the subset of features;
using the specific model of the second systematic position error along with the specific model of the first systematic position error to modify the calculated positions of the one or more features.

6. The method of claim 1 further including:
using the specific model of the systematic position error and the calculated positions of the one or more features to calculate expected deviations of the positions of the one or more features from the calculated positions of the one or more features.

7. The method of claim 6 wherein the one or more features are not included in the subset of features.

8. The method of claim 1 further including:
using the model of the first systematic position error and the calculate positions of the one or more features to calculate expected deviations of the positions of the one or more features from the calculated positions of the one or more features;
using the calculated expected deviations to determine the smallest inclusive area of the substrate, centered at a calculated position of any particular feature, that contains the particular feature; and
measuring an observable property of a feature by measuring the observable property within an area corresponding to the determined smallest inclusive area centered at the calculated position of the feature.

9. A method for determining positions of features of a nucleic acid array having been deposited on a substrate, the method comprising:
identifying a systematic position error in measuring the positions of the features;
constructing a general model of the systematic position error;
measuring the positions of a subset of the features with known positions;
refining the general model of the systematic position error to modify the measured positions of the one or more features; and
predicting the position of at least one feature of the array that is not a member of the subset, based on a measured position of the at least one feature, using the refined general model.

10. The method of claim 9 further including selecting a set of fiducial features with known positions as the subset of features.

11. The method of claim 9 wherein the systematic position error is a first systematic position error which results from a first identified source, the method further including:
identifying a second source of systematic position error in measuring the positions of the features;
constructing a general model of the second systematic position error;
refining the general model of the second systematic position error to a specific model of the second systematic position error using the measured positions of the subset of features and the known positions of the subset of features; and
using the specific model of the first systematic position error along with the specific model of the first systematic position error to modify the measured positions of the one or more features.

12. A method for determining positions of features of a nucleic acid array on a substrate, the method comprising:
calculating positions of one or more of the features;
identifying a first systematic position error of the features which results from a first identified source;
constructing a general model of the first systematic position error;
determining the positions of a subset of the features;
refining the general model of the first systematic position error to a specific model of the first systematic position error using the determined positions of the subset of features;
using the specific model of the first systematic position error to modify the calculated positions of the one or more features;
identifying a second source of systematic position error in deposition of the features;
constructing a general model of the second systematic position error;
refining the general model of the second systematic position error to a specific model of the second systematic position error using the determined positions of the subset of features; and
using the specific model of the second systematic position error along with the specific model of the first systematic position error to modify the calculated positions of the one or more features.

13. The method of claim 12, wherein the subset of features may include up to all of the features deposited on the substrate.

14. A method for determining positions of features of a nucleic acid array on a substrate, the method comprising:
identifying a first systematic position error in measuring the positions of the features;
constructing a general model of the first systematic position error;
measuring the positions of a subset of the features with known positions;

refining the general model of the first systematic position error to modify the measured positions of the one or more features;
identifying a second source of systematic position error in measuring the positions of the features;
constructing a general model of the second systematic position error;
refining the general model of the second systematic position error to a specific model of the second systematic position error using the measured positions of the subset of features and the known positions of the subset of features; and
using the specific model of the first systematic position error along with the specific model of the second systematic position error to modify the measured positions of the one or more features.

* * * * *